United States Patent [19]

Burdge et al.

[11] Patent Number: 5,489,562
[45] Date of Patent: Feb. 6, 1996

[54] HERBICIDE COMPRISING ACIVICIN AND α-METHYL DERIVATIVES THEREOF

[75] Inventors: Ernest L. Burdge, Pennsburg; Lori A. Spangler, Churchville, both of Pa.

[73] Assignee: Rohm and Haas Company, Philadelphia, Pa.

[21] Appl. No.: 271,459

[22] Filed: Jul. 13, 1994

Related U.S. Application Data

[63] Continuation-in-part of Ser. No. 114,252, Aug. 30, 1993.

[51] Int. Cl.$^6$ .......................... A01N 43/80; C07D 261/04
[52] U.S. Cl. .......................... 504/117; 504/271; 514/378; 548/240; 548/565; 548/566; 548/572
[58] Field of Search ..................... 504/271, 117; 514/378; 548/240, 565, 566, 572; A01N 43/80

[56] References Cited

U.S. PATENT DOCUMENTS

| | | | |
|---|---|---|---|
| 3,878,047 | 4/1975 | Hanka et al. | 195/80 R |
| 4,385,924 | 5/1983 | Theobald et al. | 71/88 |
| 4,772,719 | 9/1988 | Chiarino et al. | 548/247 |
| 4,970,297 | 11/1990 | Castelhano et al. | 530/331 |
| 4,983,210 | 1/1991 | Rheinheimer et al. | 71/94 |

FOREIGN PATENT DOCUMENTS 514987  11/1992  European Pat. Off. .

OTHER PUBLICATIONS

Panek, et al., J. Am. Chem. Soc. 115, 7898–7899 (1993).
A short Efficient Total Synthesis of Acivicin and Bromo–Acivicin, D. M. Vyas, Y. Chiang and T. W. Doyle, Tetrahedron Letters, vol. 25, No. 5, pp. 487–490, 1984.
Synthesis, Chemistry and Absolute Configuration of Novel Transglutaminase Inhibitors Containing A 3–Halo–4,5–dihydroisoxazole, from Bioorganic Chemistry, 16, 335–340, 1988, Arlindo Castelhano, Roland Billedeau, Diana Pliura, Bonnie Bonaventura, Allan Krantz.
Director Synthesis of the Antitumor Agent, Exthro–a–amino–3–Bromo–4,5–Dihydroisoxazole–5–Acetic Acid, 1980, Alfred A. Hagedrom III, Bryan J. Miller, Jon. O. Magy, Tetrahedron Letters, vol. 21, pp. 229–230.
Bromonitrile Oxide [3+2] Cycloadditions In Water, John C. Rohloff, James Robinson III and John O. Gardner, Institute of Organic Chemistry, Syntex Research, Palo Alto, CA 94304, Tetrahedron Letters, vol. 33, No. 22, pp. 3113–3116, 1992.
Mechanism of Inactivation of Glutamine Amidotransferases By the Antitumor Drug L–(aS,5S)–a–Amino–3–chloro–4,5–dihydro–5–isoxazoleacetic Acid (AT–125), 1979, J. Yun Tso, Stanley G. Bower, and Howard Zalkin, vol. No. 14, pp. 6734–6738.
Enzyme Targets of Antiglutamine Agents in Cancer Chemothermapy, Advance in Enzyme Regulation, 1985, National Institute of Oncology, Budapest, Hungary, H–1122, Noemi Prajda, pp. 207–223.
Acivicin in 1985, Advance in Enzyme Regulation, Robert H. Earhart and Gary I. Neil, The Upjohn Company, Kalamazoo, Michigan, vol. 24, pp. 179–205, 1985.
Tryptophas Biosynthesis in Nicotiana Tabacum and Daucus Carota Cell Cultures: Site of Action of Inhibitory Tryptophan Analogs, J. M. Widholm, Department of Agronomy, University of Illinois, Urbana, IL, Biochim Biophys, Acta, 261 (1972), pp. 44–51.
Herbicides and Plant Metabolism, A. D. Dodge, School of Biological Sciences, University of Bath, U.K., 1989, pp. 95–112.

*Primary Examiner*—S. Mark Clardy
*Attorney, Agent, or Firm*—Clark R. Carpenter

[57] ABSTRACT

A herbicidal composition having acivicin, its derivatives or salts or combinations thereof as its active component.

A process for controlling unwanted plants comprising applying a herbicidally effective amount of acivicin, its derivatives or salts or combinations thereof to the unwanted plant.

21 Claims, No Drawings

HERBICIDE COMPRISING ACIVICIN AND α-METHYL DERIVATIVES THEREOF

This application is a continuation-in-part of application Ser. No. 08/114,252, filed Aug. 30, 1993.

This invention relates to a herbicidal composition containing acivicin, its derivatives or salts or combinations thereof. This invention also relates to a process for controlling unwanted plants by applying a herbicidally effective amount of acivicin, its derivatives or salts or combinations thereof to unwanted plants.

BACKGROUND OF THE INVENTION

Acivicin is obtained from the fermentation broth of *Streptomyces sviceus*. It has been used in the treatment of certain mammalian cancers such as human lung and breast carcinoma xenografts and in mouse leukemias.

It is an object of this invention to provide a herbicidal composition containing, as its active component, acivicin, or its derivatives or salts or combinations thereof.

Another object of this invention is to provide a process for controlling unwanted plants by applying a herbicidally effective amount of acivicin, its derivatives or salts thereof and combinations thereof to the unwanted plants.

Still another object of this invention is to provide an herbicidal composition which is selectively herbicidally active to unwanted plants.

Other objects and advantages will become apparent from the following more complete description and claims.

SUMMARY OF THE INVENTION

This invention contemplates a herbicidal composition comprising a herbicidally effective amount of acivicin, its derivatives or salts or combinations thereof and an agriculturally acceptable carrier therefor.

This invention also contemplates a process for controlling unwanted plants comprising the step of applying a herbicidally effective amount of acivicin, its derivatives or salts or combinations thereof to the unwanted plant.

DETAILED DESCRIPTION

Acivicin is represented by the following formula:

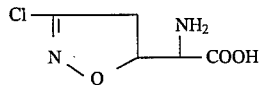

Acivicin, its derivatives or salts may be represented by the following formula:

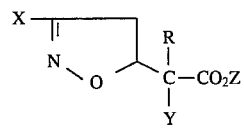

wherein Y is selected from hydrogen, amino, ammonium or mono-, di-, or trialkylammonium and an agronomically acceptable anion, or an optionally protected peptide of one or more amino acids;

R is methyl or hydrogen;

X is a halo or cyano group or sulfonate group of the formula $OSO_2R^1$ where $R^1$ is an alkyl group of from 1 to 4 carbon atoms or a phenyl ring which may be substituted anywhere on the ring.

Z is hydrogen or an agronomically acceptable cation or a carboxyl protecting group;

Y may be a hydrogen, amino, ammonium salt, such as ammonium chloride, mono-, di-, or tri-alkyl ammonium salt, or an optionally protected peptide of one or more amino acids.

When Y is an ammonium salt or an alkyl ammonium salt, the anion is an agronomically acceptable anion such as a chloride, bromide, iodide, sulfonate, carboxylate, phosphate and the like.

When Y is a mono-, di-, or tri-alkyl ammonium salt, the alkyl portion of the salt may have from 1 to 4 carbon atoms. The alkyl portion of the mono-, di-, or tri ammonium salt may each be methyl, ethyl, propyl, including isopropyl, and butyl.

Y may also be an optionally protected peptide of one or more alpha amino acids.

As used herein, the term "alpha amino acid" includes the principal naturally occurring as well as the commercially available amino acids and optical isomers thereof. Typical examples of such amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, 5-hydroxytryptophan, 4-chlorophenylalanine, 4-fluorophenylalanine, 4-iodophenylalanine, 3,4-dihydroxyphenylalanine, 3-methoxy-4-hydroxyphenylalanine, homophenylalanine, phenylglycine, o-, m-, and p-tyrosine, tryptophan, glutamine, asparagine, proline and hydroxyproline.

An amino acid residue comprises a portion of the peptide. An amino acid residue is an amino acid radical —$C(O)CH(R^3)NHP$ (P being the protective group), wherein $R^3$ is an amino acid side chain.

Exemplary of such antino acid residues are glycyl, alanyl, glycylglycyl, alanylalanyl, glycylalanyl, alanylglycyl and the like.

When the peptide is a protected peptide of the terminal amino acid, then such "N-Protecting groups" for amine functionalities of amino acids, at the peptide N-terminal, or on amino acid side chains are well known in the art. An exemplification of known amino N-protecting groups is included in The Peptides, E. Gross and J. Meienhofer, Eds., 3, Chapter 1, Academic Press, New York (1981); Protective Groups in Organic Synthesis, T. W. Greene, J. Wiley and Sons, New York, Chapter 7, (1981); and Chemistry of the Amino Acids, J. P. Greenstein and M. Winitz, J. Wiley and Sons, New York, 2, pp. 885–924 (1961). Typical of such protecting groups include Boc, CBZ, Fmoc, Phthaloyl, benzoyl, mesyl, tosyl and the like.

X is a halo or cyano group or a sulfonate group of the formula $OSO_2R^1$ wherein $R^1$ is an alkyl group of from 1 to 4 carbon atoms such as methyl, ethyl, propyl or butyl or a phenyl ring which may be substituted anywhere on the ring with groups such as $C_1$–$C_4$ alkyl, halo such as chloro, iodo, fluoro or bromo, nitro, cyano and the like.

Z may be hydrogen. Z may also be an agronomically suitable cation such as lithium, sodium, potassium, calcium, and the like. Z may also be an ammonium cation or a mono, di-, or tri-, alkyl ammonium cation where the alkyl group has from 1 to 4 carbon atoms such as methyl, ethyl, propyl and butyl. It should be understood however, that when the alkyl ammonium cation is a di- or tri-alkyl cation, the alkyl groups may be the same or different.

Z may also be a trialkylsulfonium group wherein the alkyl group has from 1 to 4 carbon atoms such as trimethylsulfonium and the like.

Z may also be a carboxyl protecting group which is capable of releasing the free carboxylic acid. Exemplary of such carboxyl protecting groups are methoxy methyl ester and other substituted methyl esters, 2-substituted ethyl esters, t-butyl esters, thiol esters and the like. Such protective groups are described in "Protective Groups In Organic Synthesis", T. W. Greene, John Wiley, New York, N.Y. (1981) pages 152– 192.

Typical compounds encompassed by the present invention include the following in Table 1. The letters used in the following table conform to those used in the specification and claims and have the definitions set forth in the specification and claims.

TABLE 1

| Compound No. | X | Y | Z | R |
|---|---|---|---|---|
| 1 | Cl | NH2 | H | H |
| 2 | Br | NH2 | H | H |
| 3 | Cl | NH3+Cl− | H | H |
| 4 | Br | NH3+Cl− | H | H |
| 5 | Cl | H | H | H |
| 6 | Br | H | H | H |
| 7 | Cl | NH2 | Na | H |
| 8 | Br | NH2 | Na | H |
| 9 | Cl | NH2 | K | H |
| 10 | Br | NH2 | K | H |
| 11 | Cl | NH2 | NH4+ | H |
| 12 | Br | NH2 | NH4+ | H |
| 13 | Cl | H | H3N+CH(CH3)2 | H |
| 14 | Br | H | H3N+CH(CH3)2 | H |
| 15 | Cl | H | Na | H |
| 16 | Br | H | Na | H |
| 17 | Cl | NH2 | H | CH3 |
| 18 | Br | NH2 | H | CH3 |
| 19 | Cl | NH3+Cl− | H | CH3 |
| 20 | Br | NH3+Cl− | H | CH3 |
| 21 | Cl | NH2 | Na | CH3 |
| 22 | Br | NH2 | Na | CH3 |
| 23 | Cl | NH2 | H3N+CH(CH3)2 | CH3 |
| 24 | Br | NH2 | H3N+CH(CH3)2 | CH3 |

The acivicin derivatives or salts may be prepared by conventional synthesis routes. For example, dibromoformaldoxime is the starting material for the preparation of all of the compounds listed in Table 1. Dibromoformaldoxime may be prepared by dissolving glyoxylic acid and hydroxylamine hydrochloride in water. To this is added sodium bicarbonate and methylene chloride. Sufficient water is then added to dissolve the salts and the mixture is cooled in an ice water bath while stirring. A solution of bromine in methylene chloride is prepared and is added to the first solution at a rate which keeps the temperature of the solution below 10° C. The reaction mixture is stirred for several hours at a temperature of 5° C. and the aqueous and organic layers are then separated from one another. The aqueous layer is then extracted three times with cold methylene chloride. The product, dibromoformaldoxime is in the organic layer. The methylene chloride of the organic layer is then removed to yield a crude solid which is then recrystallized from hexane to yield dibromoformaldoxime.

A 3-bromo-4,5-dihydroisoxazole is prepared by dissolving a water soluble vinylic dipolarophile (such as vinyl glycine or vinyl acetic acid) in water and treating it with about an equivalent of dibromoformaldoxime. The mixture is then treated with a solid mild base, such as sodium bicarbonate or sodium acetate, at a rate such that the pH of the reaction mixture is maintained between 3 and 5. Additional dibromoformaldoxime may be added until the dipolarophile is consumed as evidenced by thin layer chromatography or high performance liquid chromatography or other suitable monitoring methods. The aqueous solution is then washed with ethyl ether and the water is then removed. The product, 3-bromo-4,5-dihydroisoxazole is then purified by appropriate means, such as flash column chromatography on silica gel or ion exchange chromatography.

The 3-bromo-4,5-dihydroisoxazoles may be converted to 3-chloro-4,5-dihydroisoxazoles by dissolving the 3-bromo-4,5-dihydroisoxazole in water, methanol or tetrahydrofuran and treating the solution with gaseous hydrogen chloride and an excess of solid lithium chloride. The product, 3-chloro-4,5-dihydroisoxazole is then purified by an appropriate means such as by flash column chromatography on silica gel or ion exchange chromatography.

The preparation of the acidic salts of amino substituted 3-halo-4,5-dihydroisoxazoles may be prepared by dissolving the 3-halo-4,5-dihydroisoxazole in water or in a water miscible solvent. The acid of choice is then added slowly to maintain the temperature of the reaction mixture at about room temperature. The removal of the solvent then yields the corresponding acid salts of the amino group.

The basic salts of carboxylic acid substituted 3-halo-4,5-dihydroisoxazoles may be prepared by dissolving the 3-halo-4,5-dihydroisoxazole in water or a water miscible solvent. The solution is then treated with the base of choice (e.g. ammonia, ammonium hydroxide, an amine, a mono-, di-, or tri-alkylamine or a metal hydroxide) at a rate which is designed to keep the temperature of the reaction mixture at about room temperature. Removal of the solvent then yields the corresponding salts of the carboxylic acid.

In general, the compounds of this invention can be applied as herbicidal sprays by methods commonly employed, such as conventional high gallonage hydraulic sprays, low gallonage sprays, air blast spray, and dusts.

The herbicidal compositions may be formulated as wettable powders, emulsifiable concentrates, dusts, granular formulations, aerosols, or flowable emulsion concentrates. In such formulations, the herbicidal compounds are extended with a liquid or solid carrier and, when desired, suitable surfactants are incorporated. It is usually desirable, particularly in the case of foliar spray formulations, to include adjuvants, such as wetting agents, spreading agents, dispersing agents, stickers, adhesives and the like in accordance with agricultural practices. Such adjuvants are known in the art and may be found in John W. McCutcheon, Inc. publication "Detergents and Emulsifier Annual".

In general, the compounds of this invention can be dissolved in certain solvents such as dimethyl sulfoxide, acetonitrile, acetone, dilute aqueous acid (1–10%), methanol and water and the like and such solutions may be extended with water. The concentrations of such solutions can vary from about 1% of active component to about 90% of active component with a preferred range being from about 5% to about 50%, all percentages being by weight of the solution.

For the preparation of emulsifiable concentrates, the herbicidal composition may be dissolved in a suitable organic solvent, or mixtures of solvents, together with an emulsifying agent which permits dispersion of the composition in water. The concentration of the active ingredient in such emulsifiable concentrates is usually from about 10% to about 90%, by weight, and in flowable emulsion concentrates, this may be as high as about 75%.

Wettable powders suitable for spraying may be prepared by admixing the herbicidal composition with a dispersing agent and a finely divided solid, such as clays, inorganic silicates and carbonates, and silicas and optionally incorporating wetting agents and sticking agents in such formulations. The concentration of active ingredients in such formulations is usually in the range of from about 20% to about 98%, preferably from about 40% to about 75% (by weight).

Dusts may be prepared by mixing the herbicidal composition with finely divided inert solids which may be organic or inorganic in nature. Materials useful for this purpose include botanical flours, silicas, silicates, carbonates and clays. One convenient method of preparing a dust is to dilute a wettable powder with a finely divided carrier. Dusts concentrates containing from about 20% to about 80%, by weight, of the active ingredient may be commonly made and subsequently diluted to from about 1%, by weight, to about 10%, by weight use concentration.

In preparing the herbicidal compositions according to this invention, one or more of acivicin, its derivatives or salts may be combined with one another.

In practicing the process of this invention, the herbicidal composition according to this invention is applied in an effective amount in order to remove or control unwanted plants. Such an effective amount may vary from about 1000 g. to about 5000 g. per hectare.

The composition may be applied in the form described above, for example, as a dust, granules or a foliar spray.

In the examples which follow, acivicin, its derivatives, or salts thereof were tested as follows:

The herbicidal activity of the compounds of the invention was evaluated using a greenhouse method of testing described below. The plant species used for testing are listed below. Abbreviations used to identify plant species are included in parenthesis.

| MONOCOT | |
|---|---|
| Foxtail (FOX) | *Setaria viridis* |
| DICOTS | |
| Nightshade (NS) | *Solanum nigrum* |
| Velvetleaf (VEL) | *Abutilon theophrasti* |

Seeds of selected plants were planted in flats or pots. The flats or pots were placed in the greenhouse and then watered. The seeds were allowed to germinate and grow for 10 to 21 days. Before application, test plants were selected for uniformity, size, and stage of development. The test plants were then treated with the test compound, returned to the greenhouse and watered. The compound to be evaluated was dissolved in an appropriate solvent, usually acetone, methanol, or water and sprayed over the flats or pots using a carrier volume equivalent to 25 to 50 gallons per acre at the rate of application in grams per hectare (g/Ha) specified in the table below. About two to three weeks after application of the test compound, the state of growth of the plant was observed. Each species was evaluated on a scale of 0–100 where 0 equals no activity and 100 equals total control or plant death. The column heading abbreviations in the tables below for the plants tested are the same as for the monocots and dicots hereinabove.

In order to more fully illustrate the nature of this invention and the manner of practicing the same, the following examples are presented:

The following table shows the results obtained for the test compound at the stated rate of application and are provided merely as illustrations and are not to be considered as limitations or restrictions of the scope of this invention which is defined by the claims.

TABLE 2

| Ex. No. | Cmp. No. | Type | g/HA | NS | VEL | FOX |
|---|---|---|---|---|---|---|
| 1 | 1 | Post | 1200 | 30 | 70 | 10 |
| 2 | 3 | Post | 1200 | 20 | 75 | 10 |
| 3 | 6 | Post | 2400 | 0 | 0 | 90 |
| 4 | 7 | Post | 1200 | 30 | 75 | 10 |
| 5 | 18 | Post | 4800 | 60 | 25 | 20 |

While this invention has been described in terms of certain preferred embodiments and illustrated by means of specific examples, the invention is not to be construed as limited except as set forth in the following claims.

We claim:

1. A compound of the formula:

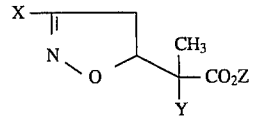

wherein Y is selected from hydrogen, amino, ammonium chloride or mono-, di-, or trialkylammonium and an agronomically acceptable anion or an optionally protected peptide of one or more amino acids;

X is a halo group; and

Z is hydrogen, sodium, or isopropyl ammonium.

2. A compound according to claim 1, wherein Y is amino, X is bromo and Z is hydrogen.

3. A compound according to claim 1, wherein Y is ammonium chloride or amino.

4. A compound according to claim 1, wherein Z is isopropyl ammonium or sodium.

5. A compound according to claim 1, wherein X is chloro or bromo.

6. A herbicidal composition comprising a herbicidally effective amount of the compound of claim 1, and an agriculturally acceptable carrier therefor.

7. A herbicidal composition comprising a herbicidally effective amount of the compound of claim 2, and an agriculturally acceptable carrier therefor.

8. A herbicidal composition comprising a herbicidally effective amount of the compound of claim 3, and an agriculturally acceptable carrier therefor.

9. A herbicidal composition comprising a herbicidally effective amount of the compound of claim 4, and an agriculturally acceptable carrier therefor.

10. A herbicidal composition comprising a herbicidally effective amount of the compound of claim 5, and an agriculturally acceptable carrier therefor.

11. A process for controlling unwanted plants comprising the step of applying a herbicidally effective amount of acivicin, its derivatives or salts or combinations thereof to the unwanted plant.

12. The process according to claim 11, wherein the herbicidal composition comprises a compound of the formula:

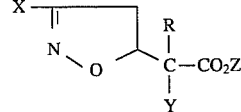

wherein Y is selected from hydrogen, amino, ammonium or mono-, di-, or trialkylammonium and an agronomically acceptable anion, or an optionally protected peptide of one or more amino acids;

X is a halo or cyano group or sulfonate group of the formula $OSO_2R^1$ wherein $R^1$ is a $C_1$ to $C_4$ alkyl group or a phenyl ring which may be substituted;

Z is hydrogen, or a carboxyl protecting group or an agronomically acceptable cation; and R is methyl or hydrogen and an agronomically acceptable carrier.

13. The process according to claim 12, wherein R is hydrogen.

14. The process according to claim 12, wherein R is methyl.

15. The process according to claim 12, wherein Y is amino, X is bromo, Z is hydrogen and R is methyl or hydrogen.

16. The process according to claim 12, wherein Y is an amino group, hydrogen, ammonium or mono-, di-, or trialkyl ammonium and an agronomically acceptable anion.

17. The process according to claim 12, wherein Z is hydrogen, sodium, or isopropyl ammonium.

18. The process according to claim 12, wherein X is a halo or cyano group.

19. The process according to claim 12, wherein Y is an optionally protected amino acid residue selected from glycyl, alanyl, glycylglycyl, alanylalanyl, alanylglycyl and glycylalanyl.

20. The process according to claim 12, wherein the herbicidal composition comprises acivicin.

21. The process according to claim 12, wherein X is a cyano or halo group.

* * * * *